United States Patent [19]

Jones

[11] 4,313,008

[45] Jan. 26, 1982

[54] SYNTHESIS OF S-3-CHLORO-1,2-PROPANEDIOL

[75] Inventor: Haydn F. Jones, Reading, England

[73] Assignee: Tate & Lyle Ltd., England

[21] Appl. No.: 39,894

[22] Filed: May 17, 1979

Related U.S. Application Data

[63] Continuation of Ser. No. 835,326, Sep. 21, 1977, abandoned.

[30] Foreign Application Priority Data

Sep. 30, 1976 [GB] United Kingdom ............... 40650/76

[51] Int. Cl.³ ....................... C07C 29/14; C07C 31/20
[52] U.S. Cl. .................................... 568/844; 568/866; 568/388; 568/460; 568/392; 424/343; 568/676; 568/600; 560/30
[58] Field of Search ............................... 568/844, 846

[56] References Cited

PUBLICATIONS

Guthrie et al., Introduction to Carbohydrate Chemistry, pp. 84–86.
Whistler et al., Methods in Carbohydrate Chemistry, Academic Press, New York, 1963, vol. II, p. 67.
Pigman, The Carbohydrates, Academic Press, New York, 1957, pp. 215–219, 346–349.
Weininger, Contempory Organic Chemistry, Holt Rinehart & Winston Inc., 1972, p. 262.

Primary Examiner—Howard T. Mars
Attorney, Agent, or Firm—Ostrolenk, Faber, Gerb & Soffen

[57] ABSTRACT

The S-enantiomer of 3-chloro-1,2-propanediol is prepared by reaction of a chlorodeoxy-D-saccharide having the partial structure.

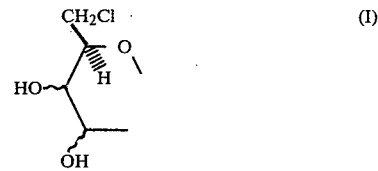

to cleave the glycol, reduce the aldehyde so formed to an alcohol, and hydrolyse the alcohol under mild acidic conditions.

14 Claims, No Drawings

SYNTHESIS OF S-3-CHLORO-1,2-PROPANEDIOL

This is a continuation of application Ser. No. 835,326, filed Sept. 21, 1977 now abandoned.

This invention relates to the synthesis of the S-enantiomer of 3-chloro-1,2-propanediol.

1-Chloropropane-2,3-diol, trivially named α-chlorohydrin, has male anti-fertility action when administered orally. Much attention has been given to the mode of action of this compound and related materials. The major site of action of α-chlorohydrin appears to be on the spermatozoa themselves in the epididymis and particularly in the *cauda epididymis,* and the action ceases soon after dosage is stopped. However, the toxicity of the compound is too high for routine use in humans, although some animal applications have been considered.

The compound previously known and tested is a racemic mixture of the S- and R-isomers. As is often the case in biologically active compounds, the activities and toxicities of the two enantiomers are different. It has been reported (Robinson, Chemistry and Industry, 1976 page 652) that the R-isomer is devoid of male anti-fertility activity and more toxic than the racemate in rats. Accordingly, the S-isomer is correspondingly more active and less toxic than the racemate. Indeed, Jackson et al (Chem.-Biol Interactions, 17 (1977) 117–120) have subsequent to the present invention shown that the S-enantiomer has twice the activity of the racemate.

In view of the superior activity and reduced toxicity of the S-isomer, it is of considerable interest as a male anti-fertility agent.

Conventional methods of obtaining the pure enantiomers of a compound such as α-chlorohydrin generally involve the resolution of the racemate, for example, by crystallisation or chromatography of the brucine salt of the phthalic acid half ester, or the menthyl carbamoyl ester.

Resolution procedures of this type are tedious and subject to difficulties. Separation of the mixture of diastereomers is sometimes a problem and also it is not always possible to define the absolute configurations of the resulting enantiomers without a considerable amount of additional work.

There is thus a need for a simple stereospecific synthetic route to the S-enantiomer.

We have now found that certain sugar derivatives of known stereochemistry can be converted by a simple 3-stage process into S-3-chloro-1,2-propanediol in a stereospecific manner in good yields.

According to the present invention, we provide a process for the production of S-3-chloro-1,2-propanediol, comprising reaction of a chlorodeoxy-D-saccharide of the partial general formula

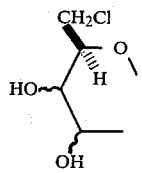
(I)

with a reagent serving to cleave the glycol grouping to provide two aldehyde groupings, to yield a derivative of the partial general formula

(II)

reduction of this derivative under mild, non-acidic conditions to an alcohol of the partial general formula

(III)

and mild acid hydrolysis of the alcohol of formula (III) to yield S-3-chloro-1,2-propanediol.

The reagent serving to cleave the glycol grouping is conveniently an alkali metal periodate, e.g. sodium periodate, or lead tetraacetate. In the case of a D-saccharide containing three adjacent hydroxyl groups, a periodate will cleave both glycol pairs to give two aldehydes and one molecule of formic acid.

The reduction of the aldehyde of formula (II) is conveniently effected by an alkali metal borohydride, e.g. sodium borohydride. Alternatively, a Raney nickel catalysed hydrogenation can be used.

The mild acid hydrolysis may be achieved using a very dilute aqueous acid, although it is preferable to contact the alcohol of formula (III) with a solid acid, such as an acid resin, e.g. Amberlyst 15, or silica gel. Mild conditions are necessary to prevent degradation.

In general, the conditions for the glycol cleavage, reduction and acid hydrolysis may be those used in the well-known Smith degradation.

The above definition outlines the process according to the present invention in general terms.

More particularly, we provide a process for the production of S-3-chloro-1,2-propanediol comprising reaction of a chlorodeoxy-D-monosaccharide or chlorodeoxy-D-oligosaccharide of the general formula

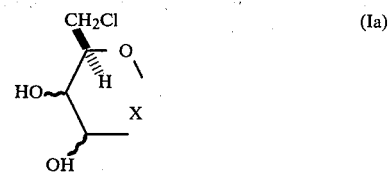
(Ia)

(in which X represents a group of the formula —[CH(OH)]$_n$—CH(R)— or

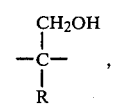

where n represents 0 or 1, and R represents an alkoxy, aralkoxy or aryloxy group or a sugar grouping) with a periodate or with lead tetraacetate to give a dialdehyde of the general formula

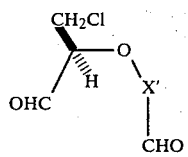
(IIa)

(in which X' represents a group of the formula —CH(R')— or

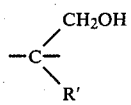

where R' is as defined above for R, or represents a glycol-cleaved derivative of a sugar grouping); reduction of the dialdehyde of formula (II) with a mild reducing agent to give a diol of the general formula

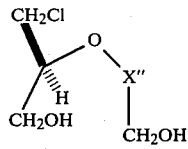
(IIIa)

(in which X" represents a group of the formula —CH(R")— or

where R" is as defined above for R, or represents a reduced, glycol-cleaved derivative of a sugar grouping); and mild acid hydrolysis of the diol of formula (IIIa) to yield S-3-chloro-1,2-propanediol.

The D-saccharide of the partial general formula (I) or the general formula (Ia) thus conveniently comprises any D-aldohexopyranoside, D-aldopentofuranoside or D-ketohexofuranoside. Where X in formula (Ia) represents —[CH(OH)]$_n$—CHR— and n=1, the saccharide can be represented by the general formula

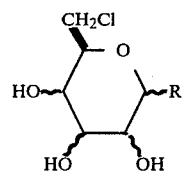
(IV)

When n=0, however, the saccharide has the general formula

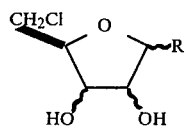
(V)

Where X in formula (Ia) represents

the saccharide has the general formula

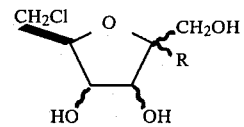
(VI)

In general, any D-saccharide capable of giving a chlorodeoxy derivative of the partial formula (I) can form the basis of the present invention. Thus, D-glucose, D-galactose, sucrose, D-fructose, D-mannose, lactose and raffinose are examples of typical D-saccharides which give appropriate chlorodeoxy derivatives of partial formula (I).

Of the compounds of formula (Ia), those in which R represents a methoxy group (methyl glycosides) or a phenoxy, benzyloxy or trityloxy group are of interest, especially methyl 6-chloro-6-deoxy-glucopyranoside.

Where R represents a sugar grouping, the chlorodeoxy-D-disaccharide used as the starting material may be any chlorodeoxy-D-oligosaccharide, e.g., a chlorodeoxy-D-saccharide having 2–10 saccharide rings, such as a chlorodeoxy-D-disaccharide, chlorodeoxy-D-trisaccharide, etc., the sugar ring(s) R" being removed and possibly broken down during the reaction sequence. Thus, for example 6-chloro-6-deoxysucrose of the formula

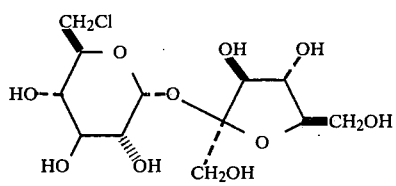
(VII)

will give a compound of the general formula IIIa having the particular structure

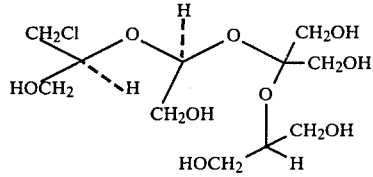
(VIII)

which, on mild acid hydrolysis, yields S-3-chloro-2,3-dihydroxypropane, together with dihydroxyacetone glycerol, and hydroxyacetaldehyde.

In a preferred embodiment of the process according to the present invention, the starting material has the general formula

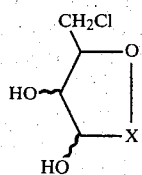
(Ia)

(in which X represents a group of the formula —[C-H(OH)]$_n$—CH(OR)— where n represents 0 or 1 and R represents a D-deoxysugar grouping also containing a partial structure of formula (I)

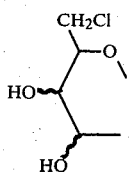
(I)

whereby two molecules of S-3-chloro-1,2-propanediol are produced from each molecule of starting material.

An example of such a starting material is 6,6'-dichloro-6,6'-dideoxysucrose of the formula

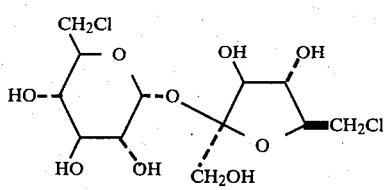
(IX)

This compound, on glycol fission with a periodate yields a compound of the formula

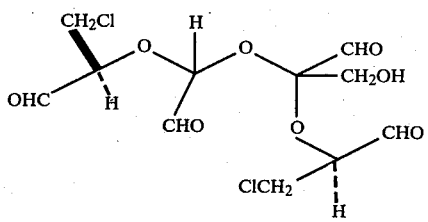
(X)

which, on reduction yields a compound of the formula

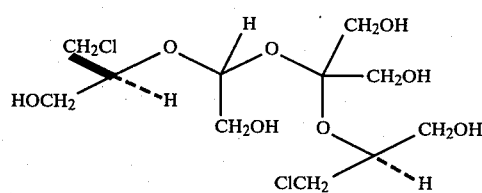
(XI)

which on mild acid hydrolysis, yields two molecules of S-3-chloro-1,2-propanediol together with hydroxacetaldehyde and dihydroxyacetone.

The process according to the present invention thus yields the S-enantiomer in a stereospecific manner, together with by-products which are easily removable. In general, the by-products are simple alcohols, hydroxyketones and hydroxyaldehydes. These by-products can be removed from the desired product by simple techniques such as distillation or chromatography.

The chlorodeoxy starting materials of partial formula (I) and general formula (Ia), may be prepared from the corresponding D-saccharides by simple techniques known in the art.

Starting materials of the general formula (Ia) in which R represents an alkoxy, aralkoxy, or aryloxy group are conveniently prepared by reaction of the corresponding glycoside of formula

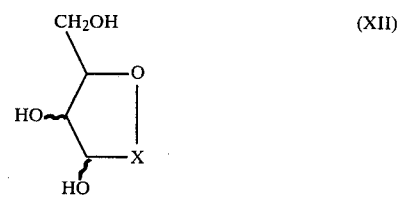
(XII)

(in which X represents a group of the formula —[C-H(OH)]$_n$—CH(R)— or

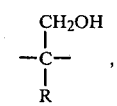

where n represents 0 or 1, and R represents an alkoxy, aralkoxy, or aryloxy group) with a sulphonyl halide reagent such as methane sulphonyl chloride in DMF, whereby the starting material of formula (Ia) is formed directly, or p-toluene sulphonyl chloride in pyridine, in which case the corresponding tosyl-derivative is formed. This tosyl-derivative is then per-O-acylated, for example by treatment with acetic anhydride in pyridine, and treated with a source of chloride ions and then deacylated. (See, for example, Methods in Carbohydrate Chemistry Vols. I, II and VI Academic Press 1962, 1963 and 1972).

The methane sulphonyl chloride treatment can also be used to prepare dichloro-dideoxy sugars of the general formula (Ia) described above, in which R represents a D-sugar grouping containing a partial structure of formula (I), for example 6,6'-dichloro-6,6'-dideoxysucrose (of formula IX). In this case, there is more than one primary hydroxy group to be chlorinated, as opposed to the simple monosaccharides of formula XII which have only one primary hydroxy group. The inclusion in the molecule of more than one primary hydroxy group means that problems can arise with separation of the possible mixture of monochloro, dichloro and trichloro products which is possible. A process for preparing 6,6'-dichloro-6,6'-dideoxysucrose dideoxysucrose itself, by this method, is described and claimed in our British patent specification No. 1430288, and this method is applicable to the production of other dichloro-dideoxysugars of this type.

The S-enantiomer of α-chlorohydrin prepared by the process according to the present invention exhibits a higher anti-fertility activity in the male rat, coupled with a considerably reduced toxicity. The therapeutic index is thus considerably higher than that of the racemate, thus rendering the S-enantiomer of considerable interest as a male anti-fertility agent.

The spermicidal activities of the S and R-enantiomers and the racemate have been investigated by an in vitro test involving measurement of inhibition of glycolysis in ram testicular sperm. In this test, the sperm, suspended in physiologically buffered saline, were incubated with the test compound for 30 minutes. 2 Millimolar $U^{14}C$-D-glucose was then added and the incubation was continued for a further 2 hours. $^{14}CO_2$ emission was monitored and also the level of lactate. The following Table shows the results obtained; the results are expressed as percentages of the control figures with no added α-chlorohydrin.

Inhibition of glycolysis in ram testicular sperm by the optical isomers of α-chlorohydrin

| Concentration mM | S-α-chlorohydrin | | RS-α-chlorohydrin | | R-α-chlorohydrin | |
|---|---|---|---|---|---|---|
| | $^{14}CO_2$ | Lactate | $^{14}CO_2$ | Lactate | $^{14}CO_2$ | Lactate |
| 0.03 | 94.3 | 56.3 | 91.0 | 80.0 | — | — |
| 0.06 | 83.6 | 37.8 | 99.3 | 37.1 | — | — |
| 0.10 | 51.2 | 19.5 | 95.6 | 25.6 | — | — |
| 0.30 | 4.8 | 2.1 | 19.9 | 1.9 | — | — |
| 0.60 | — | — | — | — | — | — |
| 1.00 | — | — | — | — | — | — |
| 10.00 | — | — | — | — | 112.6 | 73.2 |

From these preliminary results, it is clear from the $^{14}CO_2$ figures that the S-enantiomer exhibits an activity considerably higher than that of the RS-racemate. In contrast, the R-enantiomer is virtually inactive.

Subsequent work by Jackson et al (loc. cit.) has indeed confirmed these findings by showing that a single dose of 12.5 mg/kg in the rat produced a similar degree of infertility to that produced by a single dose of 25 mg/kg of a 50:50 S and R mixture.

According to a further feature of the present invention, therefore, we provide pharmaceutical compositions containing S-3-chloro-1,2-propanediol in the absence of R-3-chloro-1,2-propanediol together with a pharmaceutical carrier of excipient. The compositions according to the present invention can be formulated for medical and/or contraceptive use in humans, or for vetinary administration. The compositions may be formulated for administration by any convenient route, in particular for oral administration. Suitable dosage forms thus include tablets, capsules and other dosage unit formulations.

We have also found that intermediates of the general formula

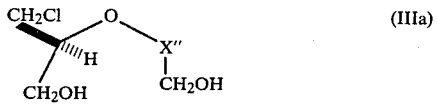
(IIIa)

(as defined above) also show anti-fertility activity. Compounds of formula (IIIa) in which X" is a group

are of particular interest, for example the compound in which R represents a methoxy group, namely 2S,4S-4-chloromethyl-2-methoxy-3-oxapentane-1,5-diol. According to yet a further feature of the present invention, we thus provide compounds of the general formula (IIIa) as defined above, having male anti-fertility activity, and compositions containing them.

The following Examples illustrate the invention further.

EXAMPLE 1

(a)
(2S,4S)-4-chloromethyl-2-methoxy-3-oxa-1,5-pentanediol

To an ice-cold solution of methyl 6-chloro-6-deoxy-α-D-glucopyranoside (23.5 g) in water (250 ml) was added a solution of sodium periodate (47.4 g) in water (250 ml). The resulting solution was stirred at room temperature for 2 hours. Evaporation of the solvent at 40° under vacuum yielded a semi-solid mass which was extracted with ethanol (3×200 ml), and the combined extracts were evaporated to give a syrup (26 g).

A solution of this product in aqueous ethanol (200 ml) was added slowly with stirring to a solution of sodium borohydride (10.4 g) in water (800 ml). After storage overnight at room temperature, the solution was treated with a little glacial acetic acid (ensuring that the pH did not fall below 7). The syrup remaining after evaporation (40°/vacuum) was dissolved in methanol and the solvent was removed by evaporation under vacuum. This process was repeated thrice, and a solution of the resulting syrup in dichloromethane was dried (Mg $SO_4$), filtered and evaporated to give a colourless, odourless syrup (19.85 g; 97.3%). The product showed one spot on thin-layer-chromatography ($R_f$ 0.8; silica gel; ethylacetate:ethanol:water, 45:5:3; charring with $H_2SO_4$). In order to be certain of the purity of the product, it was eluted from a column of silica gel with 'AR' chloroform, and evaporation of the fractions containing the product gave a clear syrup, $[\alpha]_D^{20} -16.7°$, $[\alpha]_{365}^{20} -43.8°$ (c 1.0, chloroform).

Analysis: Calc. for $C_6H_{13}ClO_4$: C, 39.0; H, 7.1; Cl, 19.2%: Found: C, 39.3; H, 7.2; Cl, 19.3%.

The mass spectrum showed, inter alia, ions at $m/e$ 153 ($^{37}Cl$ ion at 155) and 93 ($^{37}Cl$ ion at 95).

(b) Characterisation of
(2S,4S)-4-chloromethyl-2-methoxy-3-oxa-1,5-pentanediol by formation of the
1,5-di-O-(4-chlorophenyl)carbamate A solution of the diol (1.0 g) in dry pyridine (30 ml) was treated with a solution of 4-chlorophenyl isocyanate (2.0 g) in dry dioxan (20 ml). The resulting solution was maintained at reflux for 1.5 hours, cooled, and then treated with a few drops of methanol. The reaction mixture was then poured onto ice, and the solid product was filtered off, washed with water and dried. Crystallisation from hot ethanol gave the pure di-carbamate (2.60 g: 99%), m.p. 115°, $[\alpha]_D^{20} -14.3°$ Analysis: Calc. for $C_{20}H_2,Cl_2N_2O_6$: C,48.9; H, 4.3;Cl, 21.6; N, 5.7: Found: C. 49.2; H, 4.2; Cl, 21.5; N, 5.9%.

(c) (S)-3-chloro-1,2-propanediol

A solution of (2S,4S)-4-chloromethyl-2-methoxy-3-oxa-1,5-pentane-diol (14.70 g) in water (150 ml) containing a suspension of Amberlyst 15 (H+) resin (0.5 g) was maintained at reflux temperature for 2 hours. After this period g.l.c. (3% ASl, 50% phenyl, 50% cyanopropylsilane on Gas Chrom Q, programme 1 min. at 105°, then 16°/min. to 190° C., f.i.d.) showing no starting material remaining and a peak corresponding to that of standard racemic α-chlorohydrin. The solution was cooled, filtered and concentrated on a rotary evaporator at 40°, and the syrupy product was then applied to a column of silica gel (100 g), and elution was effected with ethyl acetate:ethanol:water (45:5:3). Fractions were examined by g.l.c., and the middle fraction of those containing α-chlorohydrin was evaporated to give a clear syrup (4.50 g; 52%) which was distilled (80°/0.5 mm Hg). The product had $[\alpha]_D^{20} + 7.3°$ (c, 1.0, water) (compare $[\alpha]_D^{30} 6.3$ (c, 2.03 ethanol) found by Jackson et al (loc. cit.)). The mass spectrum showed, inter alia, ions at $m/e$ 79 and $m/e$ 81. The corresponding R-enantiomer (prepared by a stereospecific route from methyl 2,3,5-tri-O-benzoyl-α-L-arabinofuranoside) possesses an $[\alpha]_D^{22}$ of $-6.9°$ (c, 2.0, water). The R-enantiomer obtained by Jackson and Robinson (Chem. Biol. Interactions, 13 (1976) 194 had an $[\alpha]_D^{22}$ of $-7.5$ (methanol).

EXAMPLE 2

Sodium periodate (9.31 g) was added slowly to a cooled and stirred solution of 6,6'-dichloro-6,6'-dideoxy-sucrose (5.0 g) in water (250 ml). After stirring at room temperature for 2 hours, the solution was diluted with ethanol (750 ml) and the resulting suspension was stirred at room temperature for a further 2 hours. The suspension was then filtered and the filtrate was concentrated to a syrup (25 ml) which was diluted with water (100 ml). A solution of sodium borohydride (2.04 g) in water (50 ml) was added slowly with cooling to the solution of oxidised product. After the addition, the reaction mixture was stirred at room temperature for 20 hours, and then a few drops of acetic acid were added. Concentration in vacuo at 40° gave a semi-solid mass which was then dissolved in ethyl acetate (AR):ethanol (9:1) and eluted through a column of silica gel. Evaporation of the eluate yielded a semi-solid mass (5:1 g). T.l.c. showed that this was a mixture. The components were identified by g.l.c. to be α-chlorohydrin, dihydroxyacetone (dimer) and hydroxyacetaldehyde.

Chromatography and distillation of the product mixture gave S-3-chloro-1,2-propanediol identical with that obtained in Example 1.

I claim:

1. A process for the production of S-3-chloro-1,2-propanediol free from R-3-chloro-1,2-propanediol, comprising reacting a chlorodeoxy-D-saccharide selected from the group consisting of chlorodeoxy-D-monosaccharides and chlorodeoxy-D-oligosaccharides containing the moiety

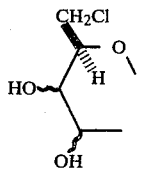 (I)

with a reagent serving to cleave the glycol grouping to provide two aldehyde groupings, to yield the corresponding derivative containing the moiety

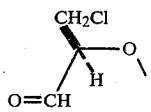 (II)

reducing this derivative under mild, non-acidic conditions to the corresponding alcohol containing the moiety

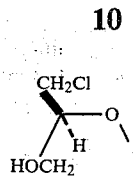 (III)

and hydrolyzing said alcohol under mild acid conditions to yield S-3-chloro-1,2-propanediol.

2. A process according to claim 1, in which said chlorodeoxy-D-saccharide is a chlorodeoxy-D-disaccharide.

3. A process according to claim 1 in which the said chlorodeoxy-D-saccharide has the general formula

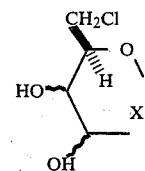 (Ia)

(in which X represents a group of the formula —[CH(OH)]$_n$—CH(R)— or

where n represents 0 or 1, and R represents a radical selected from the group consisting of alkoxy, aralkoxy and aryloxy groups and D-deoxysugar groupings containing the moiety

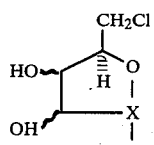 I(b)

where X represents a group of the formula

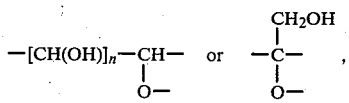

where n represents 0 or 1.

4. A process according to claim 3, in which R in formula (1a) represents a radical selected from the group consisting of methoxy, phenoxy, benzyloxy and trityloxy groups.

5. A process according to claim 3, in which the said chlorodeoxy-D-saccharide has the general formula

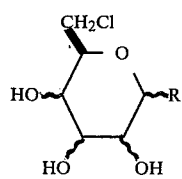 (IV)

(in which R is defined in claim 3).

6. A process according to claim 3, in which the said chlorodeoxy-D-saccharide has the general formula

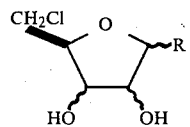 (V)

(in which R is as defined in claim 3).

7. A process according to claim 3, in which the said chlorodeoxy-D-saccharide has the general formula

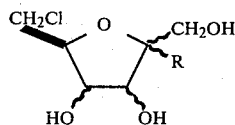 (VI)

(in which R is as defined in claim 3.

8. A process according to claim 5, in which the said compound of formula (IV) is 6-chloro-6-deoxysucrose.

9. A process according to claim 3, in which R in formula (1a) represents a D-deoxysugar grouping containing the moiety

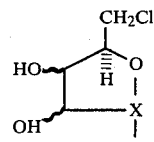 I (b)

where X represents a group of the formula

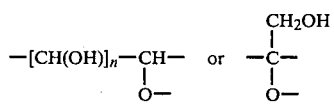

where n represents 0 or 1.

10. A process according to claim 7, in which the chlorodeoxy-D-saccharide is 6,6'-dichloro-6,6'-dideoxysucrose.

11. A process according to claim 1, in which the glycol cleaving reagent is selected from the group consisting of periodates and lead tetraacetate.

12. A process according to claim 1, in which the mild reducing agent is selected from the group consisting of alkali metal borohydrides and Raney nickel-catalysed hydrogen.

13. A process according to claim 1, in which the mild acid hydrolysis is effected using a solid acid not dissolved in the reaction medium.

14. A process for the production of S-3-chloro-1,2-propanediol free from R-3-chloro-1,2-propanediol, comprising reacting a chlorodeoxy-D-saccharide of the general formula

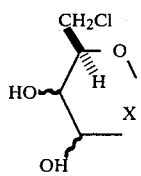 (Ia)

(in which X represents a group of the formula —[CH(OH)]$_n$—CH(R)— or

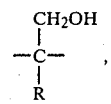

where n represents 0 or 1, and R represents a radical selected from the group consisting of alkoxy, aralkoxy and aryloxy groups and D-deoxysugar groupings containing the moiety

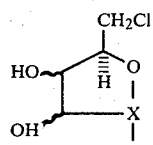 I (b)

where X represents a group of the formula

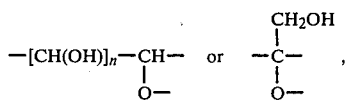

where n represents 0 or 1, with a glycol cleaving reagent selected from the group consisting of periodates and lead tetraacetate to give a dialdehyde of the general formula

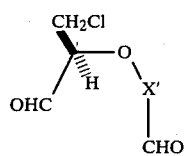 •(IIa)

(in which X' represents a group of the formula —CH(R')— or

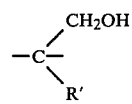

where R' is as defined above for R, or represents a glycol-cleaved derivative of a sugar grouping); reducing the dialdehyde of formula (II) with a mild reducing agent to give a diol of the general formula

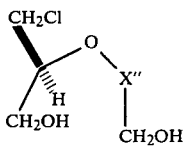 (IIIa)

(in which X" represents a group of the formula —CH(R")— or

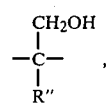

where R" is as defined above for R, or represents a reduced, glycol-cleaved derivative of a sugar grouping); and hydrolyzing the diol of formula (IIIa) under mild acid conditions to yield S-3-chloro-1,2-propanediol.

* * * * *